(12) United States Patent
Camerer, III et al.

(10) Patent No.: US 6,844,194 B1
(45) Date of Patent: Jan. 18, 2005

(54) CORN PLANT EVALUATION

(75) Inventors: William R. Camerer, III, Jersey Shore, PA (US); Nicholi L. Bajjalieh, Decatur, IL (US); Thomas R. Boyd, Jersey Shore, PA (US); James A. Breining, II, Jersey Shore, PA (US)

(73) Assignee: Doebler's Hybrids, Inc., Jersey Shore, PA (US)

(*) Notice: Subject to any disclaimer, the term of this patent is extended or adjusted under 35 U.S.C. 154(b) by 273 days.

(21) Appl. No.: 09/934,232

(22) Filed: Aug. 21, 2001

Related U.S. Application Data

(60) Provisional application No. 60/226,841, filed on Aug. 22, 2000.

(51) Int. Cl.$^7$ .............................................. G01N 33/02
(52) U.S. Cl. ............................ 436/20; 436/86; 436/95; 436/164; 436/171
(58) Field of Search .............................. 436/20, 86, 95, 436/164, 171

(56) References Cited

PUBLICATIONS

Schwab et al. "Evaluation of Corn Nutritive Value Using MILK2000", "Current Status" http://www.uwex.edu.ces/forage/wfc/proceedings2001/evaluation_of_corn_silage_types.htm.*

"Disaste Recovery. Determining moisture of immature corn silage" Aug. 1993 http://www.extension.iastate.edu/Publications/DR14.pdf.*

Jones et al. "Use of near infrared reflectance spectroscopy in forage testing", J. Dairy Sciences, 1987, 70(5), pp. 1086–1091, Abstract.*

Garrido–Varo "Use of difference near infrared reflectance spectra to extract relevant information from the spectra of agro–food products" J. Near Infrared Spectrosc., 1998, v. 6, pp. 88–95, Abstract.*

GMPRC "Reseacr Kernels", www.usgmrl.ksu.edu. Jul. 2000.*

Eigenvector Research Inc. "NIR of corn samples for standardization benchmarking", corn.met, Oct. 18, 1999.*

Illinois Fertilizer Conference Proceedings, "Monitoring Crop Stresses", Jan. 26–28, 1998.*

C. Philippeau and B. Michalet–Doreau, "Influence of Genotype and Ensiling of Corn Grain on In Situ Degradation of Starch in the Rumen", *Journal of Dairy Science*, vol. 81, No. 8, pp. 2178–2184, 1998.

G. M. Jones et al., "Use of Near Infrared Reflectance Spectroscopy in Forage Testing", *Journal of Dairy Science*, vol. 70, No. 5, pp. 1086–1091, 1987.

* cited by examiner

*Primary Examiner*—Yelena G. Gakh
(74) *Attorney, Agent, or Firm*—Philip L. Bateman

(57) ABSTRACT

A corn plant is evaluated by a six-step method. The first step is to select a population of mature corn plants to be evaluated. A limited number of representative plants from the population are then selected. The representative plants are then harvested by cutting them near the ground. The plants are then ground into a homogeneous mixture. A sample of the homogeneous mixture is then analyzed in a near infrared spectrometer. The analysis is then compared with an existing correlation between near infrared analyses and wet-test chemistry tested nutritional compositional characteristics to predict the compositional characteristics of the corn plant population.

4 Claims, No Drawings

CORN PLANT EVALUATION

CROSS-REFERENCE TO RELATED APPLICATION

This application claims the benefit of U.S. Provisional Application Ser. No. 60/226,841, filed Aug. 22, 2000.

FIELD OF THE INVENTION

This invention relates to the cultivation of corn. More particularly, this invention relates to the evaluation of whole corn plants.

BACKGROUND OF THE INVENTION

Corn is the most important crop grown in the United States and is the second largest crop grown in the world. A corn plant begins life as a seed, also known as a kernel. The kernel has three main parts: (1) an embryo, or germ, that develops into the plant; (2) an endosperm consisting primarily of starch that is used for energy by the embryo; and (3) a seed coat. After planting in the ground, the kernel develops into a seedling and then a mature plant. A mature corn plant consists of roots, an upright stalk, leaves, one or more ears (each consisting of hundreds of kernels on a cob), and a tassel. A typical corn plant grows to a height of about three meters and has a life span of about five months.

A corn plant reproduces sexually. Male sex cells from pollen released by the tassel unite with female sex cells on the cob. Most of the pollen falls on other plants, but some self-pollination typically occurs. The fertilized sex cells develop into the kernels on the cob. Unfertilized female sex cells result in empty spots on the cob.

Most corn grown in the United States is of a genetic type known as hybrid corn. Hybrid corn is produced by a lengthy breeding process which begins by growing selected corn plants under conditions where inbreeding occurs, i.e., the selected plants are fertilized only by other plants in the same selected group. The inbreeding process is continued for several generations until all the plants in the group have similar genetic compositions. The next step in the process is to cross two inbred varieties. This is accomplished by planting the two varieties in close proximity to each other and removing the tassels of one of the varieties. The plants with the removed tassels are fertilized by the other variety of plants. The resulting kernels from these plants are known as single-cross corn hybrids and have a genetic composition which is a combination of the two inbred varieties.

Corn kernels are a common food for both animals and humans. Corn kernels are separated from other portions of the corn plant during the harvesting process and typically represent approximately fifty percent of the total dry mass of the corn plant. The non-kernel portion of the corn plant represents little nutritional value to humans and similar simple-stomached animals, because it is high in fiber and other components that cannot be effectively broken down by their digestive systems. Ruminant animals, such as cattle, have complex compartmentalized stomachs that allow for the breakdown and nutritional utilization of certain plant fiber materials. As a result, the non-kernel portion of the corn plant can be used as a source of nutrients for ruminants.

Corn silage is one form by which the total corn plant has historically been utilized as a source of nutrients for ruminant livestock. The process of making corn silage, known as ensiling, begins with the harvesting of the plant at a time when the combination of yield and overall nutrient value of the whole plant is at its maximum. This is typically associated with a plant that is high in moisture and thus subject to rapid decay unless somehow stabilized. The ensiling process makes use of a natural fermentative process that results in a lowering of the pH, i.e., an increase in acidity, and removal of oxygen from the silage mass to the point that it becomes resistant to spoilage. When properly ensiled, stored, and handled, corn silage can be fed over a period of several months after harvest.

The ensiling process is a complex interaction of many factors and phenomena. First, there is a series of issues associated with the physical and chemical characteristics of the corn plant utilized. In addition, the ensiling process itself requires the proper integration of several other steps and phenomena, all of which impact the quality of the final product.

A considerable amount of variation and interaction exists relative to the factors associated with silage production and its subsequent nutritional and related economic value. As a result, a considerable amount of research effort has gone into understanding and identifying ways to improve silage quality. Much of past work has focused on evaluations of a finished, ensiled product.

The economic value of corn silage is related to its ability to serve as a source of nutrients, which in turn is related to its compositional characteristics. The compositional characteristics of corn silage are primarily a function of the compositional characteristics of the corn plant and the microbial activities associated with the ensiling process. To maximize the extraction of value from differences in corn plant compositions, the composition must be accurately described. A major impediment to the accurate compositional evaluation of corn silage has been the nature of the corn plant itself. A corn plant is an organism that is made up of many highly specialized components. These specialized components display both chemical and physical differences. Obvious to even a casual observer are the physical differences between various plant parts, such as the stalk, leaves, grain, cob, etc. This diversity of chemical and physical characteristics presents a number of challenges relative to the obtaining of truly representative samples for compositional analysis. These differences make it difficult to obtain a high degree of sample homogeneity. Sample homogeneity is especially critical in light of the relatively small quantities of sample utilized as a part of most commercially applied analytical procedures. A further confounding factor is the effect that environment has on the expression of plant characteristics. Even within a given field, i.e., population, of corn, different microenvironments may exist. If not properly addressed, this can further confound such evaluations.

Describing the characteristics of a large population, such as a field of corn, through the use of samples requires that the samples be truly representative of the aggregate population. In the case of a population of whole corn plants, the above factors represent a significant challenge to being able to obtain samples which are truly representative of the aggregate population. This issue is further magnified when considered in the context of the small quantities of samples typically utilized for laboratory analysis. Thus, the ability to obtain homogeneous samples that truly represent the above-root corn plant population from which they are obtained is critical to the compositional evaluation of whole corn plant populations. Without the ability to consistently obtain, process, and analyze truly representative samples of aggregate whole corn plants, a considerable amount of sampling error is introduced into the evaluation process. The net effect is that true advantages and improvements in whole plant compositional traits are hidden by the gray area of sample variation. As a result, progress in identifying and capturing value from such differences is stifled. This aspect continues to represent a major challenge to those trying to identify compositional differences between populations of corn plants.

One approach to dealing with a large amount of inherent sample variation is to incorporate the use of more samples to better describe the population the samples are supposed to represent. For example, one study of corn plants used twenty whole plants and forty ears. C. Philippeau and B. Michalet-Doreau, "Influence of Genotype and Ensiling of Corn Grain on In Situ Degradation of Starch in the Rumen," Journal of Dairy Science, Vol. 81, No. 8, 1998, pp. 2178–2184. Because the cost of this type of research is directly related to the expenses associated with sample procurement, processing, and analysis, addressing large inherent sample variation through increased sample numbers becomes a direct research cost issue. Accordingly, a demand exists for a process that improves the ability to obtain and analyze truly representative samples from populations of whole corn plants. Such a process would benefit the silage evaluation process by providing for both greater accuracy and precision of results while reducing the associated expenses.

SUMMARY OF THE INVENTION

The general object of this invention is to provide an improved method for evaluating whole corn plants. A more particular object is to provide a method for evaluating populations relative to their aggregate, whole plant compositional characteristics. While a primary application is the evaluation of corn varieties relative to their use in corn silage, this invention has applications wherever the need for evaluating compositional characteristics of the whole corn plant are required. Additional more particular objects are to provide a corn variety evaluation method that is more accurate, less expensive, and faster than current methods employed relative to compositional characteristics of the whole corn plant.

We have invented a method of evaluating the compositional characteristics of a whole corn plant. The method comprises: (a) selecting a population of mature corn plants to be evaluated; (b) selecting a limited number of representative plants from the population; (c) harvesting the representative plants; (d) grinding the individual representative plants into a homogeneous mixture; (e) analyzing a sample of the homogeneous mixture in a near infrared spectrometer; and (f) comparing the near infrared analysis results with an existing correlation between near infrared analyses and wet-chemistry evaluated compositional nutritional characteristics to predict the nutritional characteristics of the corn plant population.

The method is more accurate than current methods for several reasons, including its ability to: (a) obtain samples of whole corn plants that are more uniform; (b) obtain samples that are more representative of the population which they are intended to represent; (c) better address the sampling and analytical variation inherent in this type of process through an improved process for sample handling, preparation, analysis, and real-time cross-checking of analytical results; and (d) use analytical results in such a way that better estimates the economic significance of differences observed relative to animal production applications. The method is less expensive because its greater accuracy reduces the required size and scope of the evaluation process, and because the time required to physically process and analyze samples is reduced. The process is faster because the need for certain processing steps is reduced and because greater precision allows more succinct evaluations.

DETAILED DESCRIPTION OF THE INVENTION

1. The Invention in General

The invention is a six-step method for evaluating aggregate, whole plant compositional characteristics of corn plant populations. The process begins with the selection of a population of corn plants for testing. The terms "method" and "process" are used interchangeably herein. A number of representative individual plants are harvested utilizing a specific protocol. Each individual plant is then processed through the application of a novel methodology that incorporates a piece of equipment heretofore used in human food processing applications. Samples are then evaluated using a near infrared (NIR) analytical process, which enables the multiple scanning, i.e., analysis, of a relatively large portion of the sample. Critical aspects of the best use of the NIR technologies have been addressed and refined as a part of the process. Value is further extracted from the compositional information through the application of methods that translate analytical data into more meaningful economic based evaluation criteria.

2. Selecting a Population of Corn Plants for Sampling

The first step in the method of this invention is to select a population of mature corn plants for sampling. The method may be applied to a variety of types of corn plant populations. These include highly controlled experimental populations as well as populations being grown under commercial production conditions.

3. Selecting Plants to be Harvested for Evaluation

The second step in the method is to select the individual plants to be harvested for evaluation. Good sampling procedures strive for the selection of samples that accurately represent the population from which they are obtained. A major issue within a given population of corn plants is the effect that differences in microenvironment within a growing area have on plant composition. The method of this invention incorporates a procedure for sample selection that addresses distortions associated with vagaries in microenvironment within a population of corn plants.

First, the population of plants is visually surveyed for predominant plant characteristics and appropriate observations documented. A criterion for plant selection is that it must be a fair representative of the population, in other words, it must exhibit those characteristics noted as being predominant for its population. Examples of surveyed characteristics include plant height, number of ears, and height of first ear. A second requirement is that a plant must be surrounded by plants of its own type. The exception to this requirement is when plants are obtained from test plots in which single or double rows of each plant variety are grown or when individual plants are grown under highly controlled conditions, e.g., individually potted plants in a greenhouse. A third requirement is that the spacing of neighboring plants be consistent among plants selected. It is extremely important the plant selection be based upon similar sized plants with uniform plant spacing and plant characteristics relative to the population they are intended to represent.

The number of plants for each population which should be harvested will vary with the objectives of the evaluation process and the plot conditions. Critical research types of evaluations, utilizing scientifically sound statistical procedures, will require more samples than a test which attempts to identify the general compositional characteristics of a production field. Based upon experience, however, a minimum of three samples plants should be collected and processed for each replicate being evaluated.

4. Harvesting the Representative Plants

The third step of the method of this invention is to harvest the representative plants. Specific objectives to be addressed will dictate the exact stage of plant maturity at which harvest is to occur. As an example, for our silage evaluation purposes, representative plants are harvested at physiological maturity when the kernels from the majority of the plants have achieved the 50 percent milk line. Plants selected for harvest are cut at a uniform height above the ground, preferably about six inches. It is important that plants not be damaged or contaminated with other materials after they are harvested. They are preferably placed onto a clean tarp and gently carried from the field. If plants are to be stored, prior to processing and analysis, they should be stored upright in a cool, uniformly humid environment. The preferred conditions are about 50° F. and 50 percent relative humidity. These conditions deter microbial degradation and prevent damage due to moisture condensation.

5. Grinding the Plants

The fourth step in the method is to grind and mix the whole plant components. Prior to grinding, physical measurements of the plant may be taken. The individual whole plants are then ground using the following steps. If dirt contamination is a concern, the first step is to cut a one inch piece from the base of the stalk and discard it using a set of well-sharpened, spring-loaded pruning shears. If dirt contamination is not a concern, the first step is typically omitted. The next step is to husk out the ear. After husking out the ear, its weight is recorded and it is temporarily separated from the rest of the plant. After all desired plant characteristics are recorded, the ear is added back and the whole plant is ground using a bowl grinder of a size and horsepower appropriate for the thorough grinding of the plant material involved.

Bowl grinder are typically used for grinding meat products and feature a rotating bowl mounted on a pedestal. The bowl is semi-toroidal in shape, i.e., it is similar in shape to a bundt pan of the type commonly used as a mold for cakes and gelatin. An assembly of blades rotate from an arm that extends over the bowl. The blades rotate in a vertical plane (about a horizontal axis) as the bowl rotates horizontally (about a vertical axis). The material in the bowl is sliced by the sharp, thin blades with each rotation of the bowl. Unlike other types of grinders, bowl grinders have the surprising ability to cut the long, vertical fibers associated with the stalk. These fibers tend to wrap around the blades of other types of grinders. While the specific make and model of bowl grinder are not critical to the process, a preferred machine is a Kramer and Grube model 41862 cast iron bowl grinder. The stalk and ear are introduced into the running machine and processed to a physical consistency similar to that of coarsely chopped cole slaw. While the specific amount of time required should be expected to vary, the time required is typically in the neighborhood of one minute.

The grinding and mixing process is further enhanced through the careful use of a diverter. This device is cut from a flat piece of either wood or plastic and shaped to conform to the inner contour of the bowl, to which a handle is attached. The diverter is used to alternatively bunch and turn over the mass of chopped material as it immediately leaves the chopping action of the cutting blades and in preparation for the next pass through the blades. The chopping blades are extremely sharp and turn at a high rate of speed. Therefore, they represent a considerable danger to the operator if not appropriately addressed. It is thus critical that proper shielding and care should be exercised to avoid all contact with the moving cutters.

After grinding, the processed sample is collected into a plastic tub and weighed. This weight is recorded with the other plant characteristics previously mentioned.

6. NIR Analysis

The fifth step of the method is to analyze a sample of the ground and mixed material in a near infrared (NIR) spectrometer. NIR photospectrometry is used for several reasons: (1) speed; (2) cost per sample; (3) the ability to analyze a relatively large amount of sample; and (4) the nondestructive nature of the analysis allows for repeated analyses of the same sample when further verification is desirable. While the sample obtained from the method of sample preparation grinding is more homogenous than typical samples of its type, it is still not perfectly homogenous. When dealing with non-homogenous materials, the ability to analyze larger sample masses and the ability to have multiple evaluations of each sample become highly desirable. However, from a practical perspective, the costs of such procedures become an important consideration. Elements of complementary direct and indirect analytical processes have been adapted to better address these specific needs in the contest of the NIR procedure.

The NIR analysis is begun by further mixing the entire ground individual corn plant (sample) on a plastic sheet to incorporate any large and small particles that may have separated during grinding. The sample is then divided into two piles (sub-samples) of approximately equal size. Two NIR natural product cells are then packed with multiple grab portions, one holder for each of the two sub-samples. The natural product cell is a NIR sample holder with about sixteen square inches of viewing area. This type of sample holder allows for a relatively large sample size compared to that typically analyzed by "wet chemistry" methods. Sample material is consistently packed in each sample holder.

The analysis of the two sub-samples is done using an appropriately configured NIR spectrometer. A preferred spectrometer is a NIRSystems model 5000 monochromator with a sample transport mechanism. This monochromator measures the reflectance in the near infrared spectral region having wavelengths from 1100 to 2500 nanometers. Each sample holder is scanned at approximately 25 locations across the quartz face of the sample holder. Multiple scanning of the sample, in effect, represents its multiple NIR analysis. The results from this multiple scanning are then averaged.

Samples are intended to be representative of the population from which they are obtained. Where a lack of homogeneity is an issue, the identification and elimination of non-representative samples has to be addressed. Using typical procedures, this is an expensive process from both the standpoints of time and economic expense. The process of this invention incorporates a real-time comparative evaluation of samples from the same plant that allows for the rapid identification of non-representative samples, the re-sampling of subsamples and their re-analysis.

NIR results for paired subsamples from an individual plant are compared at the time of NIR analysis. If the difference between the NIR analysis for these two sub-samples exceeds pre-established limits, a third sub-sample is immediately obtained and analyzed. Differences between this sample and the two previous samples are compared to the pre-established tolerances. If one of the two differences fall within the tolerance range, results from these two samples are then utilized.

7. Use of the NIR Analysis to Predict Compositional Characteristics

The sixth step of the method is to correlate spectral results from the NIR analysis with specified compositional characteristics determined through the use of appropriate "wet-chemistry" analytical techniques. In this way, results from an NIR analysis are "translated" into estimates that approximate the probable results obtained from a series of wet-chemistry analyses. Such relationships are the basis of "indirect" analytical techniques.

It is well known that the compositional characteristics of a corn plant can be determined directly by "wet chemistry" techniques. For example, crude protein content is determined by the Kjeldahl method, fat content is determined by solvent extraction techniques, moisture content is determined by heating the sample in an oven to drive off moisture, etc. It is also well known that NIR analysis can be used to provide an indirect determination of the same properties. Approximate correlations between wet-chemistry tested compositional characteristics and NIR analyses are widely known and utilized. Often, such an existing correlation between NIR analyses and wet-chemistry tested compositional characteristics can serve as the starting point.

The "calibration" is the translator between results obtained from an NIR analysis and those obtained through wet-chemistry techniques. Thus, the robustness of the calibration is critical to the level of accuracy associated with an NIR analysis. Both physical and chemical characteristics of a sample impact the measurements of compositional characteristics by NIR. As a result, NIR calibrations must be developed for specific types of samples and the physical condition at scanning on the NIR instrument (e.g., moisture, particle size, etc.). NIR calibrations must also include the entire breadth of diversity associated with a population. In addition, such calibrations must be properly maintained through an ongoing reevaluation program. Various strategies have been employed in the past. The preferred approach is described below.

The first step is to establish a base calibration to which successive data can be added. Early duplicate samples, split and processed as described above, are analyzed by NIR and the associated spectral results stored. The duplicate samples are then sent for chemical analysis utilizing wet chemistry methodologies. All samples sent to the wet chemistry reference laboratory are sent in duplicate. Individual sub-samples are placed in separate plastic bags and identified. The sub-samples are frozen for storage and later cold shipped to the reference laboratory for wet-chemistry analysis.

For consistency it is preferred to use only one quality wet chemistry reference laboratory. When the wet-chemistry derived component values are reported, values first are compared between the two duplicate samples. When the difference between the two values of a component is less than a pre-established error tolerance limit, the paired values are averaged and the corresponding values added to the calibration database. If the difference between the two values for any one component is greater than the error tolerance limits, that data is not included in the calibration. Some samples are re-analyzed and the new values tested for difference error. If the difference value is within tolerance, the new values are only then used.

Acceptable wet-chemistry derived reference data is then paired with the corresponding NIR observations and regression equations, which correlate the two sets of observations, are developed. A partial least squared calibration method is used for the equation development. The resultant regression equation is the "calibration."

"Outliers" are NIR observations that fall beyond the scope of an existing data set. All samples are evaluated for spectral fit using the most recent calibration equation. For any sample that exceeds the predefined outlier limits, the two sub-samples are bagged and labeled separately and the pair sent to a lab for reference analysis. Each sub-sample is analyzed as a separate individual sample, one analysis for each of the two sub-samples. All reference data to be added to the calibration must pass the evaluation of difference as described above. Sample wet-chemistry derived results that meet these criteria, and the associated spectra, are added to the existing database.

Indirect analytical technologies, such as NIR, offer much greater speeds and much lower costs than typical wet chemistry methods. However, it is critical that the application of such technologies be properly supported through the on-going integration of ancillary procedures, including wet-chemistry run checks. Critical to the overall process is the development and application of such procedures. This includes not only the establishment of correlation equations, i.e., calibrations, but their ongoing maintenance as well.

Thus calibrations must continually be reevaluated and updated as necessary. To this end, portions of the NIR analyzed samples are periodically selected at random for validation analysis. Only samples that spectrally fit the previous year's calibrations, i.e., are not considered as outliers, are included in the validation set. Validation analysis samples are analyzed by wet-chemistry analysis. Differences between paired samples are evaluated as described above. Acceptable wet chemistry results are compared to those obtained from the NIR analysis. For accepted results, data from both the wet-chemistry and corresponding NIR analysis are then added to the calibration data set.

Periodically, the new data set (the combination of all previous wet-chemistry data and the corresponding NIR data, plus that from subsequently run outliers and re-validation samples) is used to recalculate the regression equations used to correlate wet-chemistry observations to those from the NIR machine. This updated calibration can then be applied to both new and previous NIR observations, stored within computer files, to project composition using the most recent data set.

8. Use of the Nutritional Characteristics Information

Analytical information about the compositional characteristics of the corn population, in and of itself, has little real value unless it can be utilized in a way to create further value. The data captured through this process is easily translated into information that is of benefit to a decision making process. The process captures compositional information that is then utilized through a series of equations to project economic benefit. This final translation of information becomes a powerful tool for those needing to make business decisions relative to the comparative use of corn varieties. It is the integration of this final step with those previously discussed which finally crystallizes the value of the process of this invention.

We claim:

1. A method of predicting the compositional characteristics of a corn plant population, the method comprising:
    (a) selecting a population of mature corn plants to be evaluated;
    (b) selecting a limited number of representative plants from the population based on visually surveyed characteristics;

(c) harvesting the representative plants;
(d) grinding the representative plants into a homogeneous mixture using a bowl grinder;
(e) analyzing a sample of the homogeneous mixture in a near infrared spectrometer; and
(f) comparing the analysis with an existing correlation between near infrared analyses and wet-chemistry tested nutritional compositional characteristics.

2. The method of claim 1 wherein at least three representative plants from the population are selected.

3. The method of claim 1 wherein the representative plants are harvested at physical maturity.

4. The method of claim 1 wherein the sample is analyzed by scanning at a plurality of locations.

* * * * *